United States Patent [19]

Chasin et al.

[11] Patent Number: 5,864,037
[45] Date of Patent: Jan. 26, 1999

[54] METHODS FOR THE SYNTHESIS OF CHEMICAL COMPOUNDS HAVING PDE-IV INHIBITORY ACTIVITY

[75] Inventors: Mark Chasin, Manalapan, N.J.; David Cavalla, Cambridge, Great Britain; Peter Hofer, Liestal, Switzerland

[73] Assignee: Euro-Celtique, S.A., Luxembourg, Luxembourg

[21] Appl. No.: 659,767

[22] Filed: Jun. 6, 1996

[51] Int. Cl.[6] ............. C07D 473/34; C07D 473/22; C07D 473/40

[52] U.S. Cl. ............. 544/118; 544/277; 544/264; 544/265

[58] Field of Search ............................................. 544/277

[56] References Cited

U.S. PATENT DOCUMENTS

| Re. 31,429 | 10/1983 | Tull et al. ............................. | 544/277 |
|---|---|---|---|
| 2,691,654 | 10/1954 | Hitchings .............................. | 260/247.5 |
| 2,844,577 | 7/1958 | Acker .................................... | 260/254 |
| 2,903,455 | 9/1959 | Strong et al. .......................... | 260/252 |
| 2,956,998 | 10/1960 | Baizer .................................... | 260/252 |
| 2,957,875 | 10/1960 | Lyttle et al. ........................... | 260/252 |
| 2,966,488 | 12/1960 | Shive et al. ........................... | 260/252 |
| 3,079,378 | 2/1963 | Schroeder et al. .................... | 260/211.5 |
| 3,135,753 | 6/1964 | Hitchings ............................... | 540/265 |
| 3,136,771 | 6/1964 | Liechti et al. ......................... | 260/296 |

(List continued on next page.)

FOREIGN PATENT DOCUMENTS

| 4707193 | 8/1997 | Australia . | |
|---|---|---|---|
| 0018136 | 10/1980 | European Pat. Off. . | |
| 0178413 | 4/1986 | European Pat. Off. . | |
| 0191313 | 8/1986 | European Pat. Off. . | |
| 0203721 | 12/1986 | European Pat. Off. . | |
| 0256692 | 2/1988 | European Pat. Off. . | |
| 0258191 | 3/1988 | European Pat. Off. . | |
| 0343643 | 11/1989 | European Pat. Off. . | |
| 0369744 | 5/1990 | European Pat. Off. . | |
| 0386675 | 9/1990 | European Pat. Off. . | |
| 0386683 | 9/1990 | European Pat. Off. ...... | C07D 473/04 |

(List continued on next page.)

OTHER PUBLICATIONS

Elion, Ciba Foundation Symp., Chem and Biol. Purines, pp. 39–49, 1957.

Ronald E. Weishaar, et al., Subclasses of Cyclic GMP–Specific phosphodiesterase and their role in regulating the effects of atrial natriuretic factor, Dept. of Pharmacology, Parke–Davis Pharmaceutical Research Division, Warner–Lambert Co. Hypertension, vol. 15, No. 5, May 1990.

"Differential modulation of tissue function and therapeutic potential selective inhibitors of cyclic nucleotide phosphodiesterase isoenzymes", C. David Nicholson, R.A. John Challiss and Mohammed Shahid, 1991, Elsevier Science Publishers Ltd. (UK), TIPS 12:19–27.

(List continued on next page.)

*Primary Examiner*—Mark L. Berch
*Attorney, Agent, or Firm*—Davidson, Davidson & Kappel, LLC

[57] ABSTRACT

Disclosed is a process for the preparation of a compound of Formula IV having the structure:

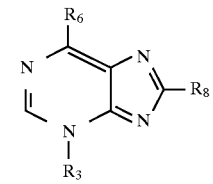

IV wherein $R_6$ is $N(R_{6a})(R_{6b})$;

$R_3$ represents a $C_{2-8}$, alkyl which is unbranched or branched and unsubstituted or substituted; $C_{3-8}$ cycloalkyl which is unsubstituted or substituted; $C_{4-8}$ cycloalkylalkyl wherein the cycloalkyl portion is unsubstituted or substituted; aryl or benzyl which is optionally unsubstituted or substituted; ar($C_{1-4}$)alkyl; a heterocyclyl group, ring optionally substituted; heterocyclyl ($C_1$–$C_4$) alkyl ring optionally substituted;

which comprises:

(a) treating a compound of Formula I:

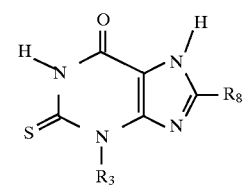

I with an effective amount of a dethionating agent to produce a compound of Formula II:

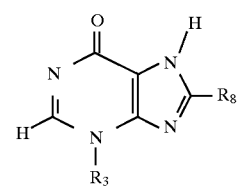

II (b) treating a compound of Formula II with an effective halogenating agent under conditions effective to produce a compound of Formula III:

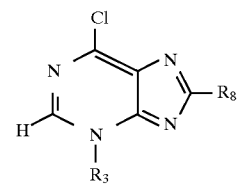

III and (c) treating a compound of Formula III with an effective aminating agent under conditions effective to produce a compound of Formula IV.

18 Claims, No Drawings

U.S. PATENT DOCUMENTS

| | | | |
|---|---|---|---|
| 3,215,696 | 11/1965 | Denayer | 260/252 |
| 3,225,046 | 12/1965 | Zwahlen | 260/252 |
| 3,262,929 | 7/1966 | Okubu et al. | 260/240 |
| 3,494,919 | 2/1970 | Collins et al. | 260/240 |
| 3,541,100 | 11/1970 | Ramirez et al. | 260/286 |
| 3,574,218 | 4/1971 | Hideg et al. | 260/293.4 |
| 3,590,029 | 6/1971 | Koch et al. | 260/211.5 |
| 3,636,039 | 1/1972 | Gruenman et al. | 260/309.7 |
| 3,674,781 | 7/1972 | Schinzel et al. | 260/240 |
| 3,706,834 | 12/1972 | Scheilenbaum et al. | 424/272 |
| 3,923,833 | 12/1975 | Gruenmann et al. | 260/340.5 |
| 3,962,452 | 6/1976 | Evans et al. | 424/272 |
| 4,025,636 | 5/1977 | Dunwell et al. | 424/269 |
| 4,025,637 | 5/1977 | Dunwell | 424/272 |
| 4,107,306 | 8/1978 | Voorhees | 424/248.51 |
| 4,167,628 | 9/1979 | Kormany | 542/454 |
| 4,233,303 | 11/1980 | Bergstrand et al. | 424/253 |
| 4,241,063 | 12/1980 | Naito et al. | 424/253 |
| 4,308,278 | 12/1981 | Schneider et al. | 424/273 |
| 4,361,699 | 11/1982 | Rasmusson et al. | 544/277 |
| 4,407,802 | 10/1983 | Graham et al. | 424/253 |
| 4,416,892 | 11/1983 | Dawson | 424/272 |
| 4,454,138 | 6/1984 | Goring | 424/253 |
| 4,469,698 | 9/1984 | Philipossian et al. | 424/253 |
| 4,616,020 | 10/1986 | Furrer et al. | 514/264 |
| 4,652,654 | 3/1987 | Verga et al. | 548/217 |
| 4,684,656 | 8/1987 | Atwal | 514/274 |
| 4,710,503 | 12/1987 | Hofer | 514/263 |
| 4,755,517 | 7/1988 | Bruns et al. | 514/263 |
| 4,769,377 | 9/1988 | Snyder et al. | 514/263 |
| 4,803,216 | 2/1989 | Appleton et al. | 514/407 |
| 4,831,152 | 5/1989 | Itoh et al. | 548/224 |
| 4,851,321 | 7/1989 | Takagi et al. | 430/264 |
| 4,868,183 | 9/1989 | Kanai et al. | 514/255 |
| 4,883,801 | 11/1989 | Nathanson | 514/263 |
| 4,925,847 | 5/1990 | Hofer | 514/263 |
| 4,965,169 | 10/1990 | Hirano et al. | 430/264 |
| 4,971,972 | 11/1990 | Doll et al. | 514/265 |
| 4,981,857 | 1/1991 | Daluge et al. | 514/263 |
| 4,988,689 | 1/1991 | Janssens et al. | 514/212 |
| 5,010,081 | 4/1991 | Hofer | 514/263 |
| 5,047,411 | 9/1991 | Takasugi et al. | 514/300 |
| 5,057,517 | 10/1991 | Johnston et al. | 514/254 |
| 5,068,236 | 11/1991 | Suzuki et al. | 514/263 |
| 5,091,431 | 2/1992 | Tulshian et al. | 514/262 |
| 5,110,818 | 5/1992 | Allgeier | 514/261 |
| 5,117,830 | 6/1992 | McAfee et al. | 128/654 |
| 5,139,921 | 8/1992 | Takagi et al. | 430/264 |
| 5,175,290 | 12/1992 | Rzeszotarski et al. | 544/267 |
| 5,175,291 | 12/1992 | Kufner-Muhl | 544/267 |
| 5,177,074 | 1/1993 | Allen et al. | 514/234 |
| 5,190,942 | 3/1993 | Poss | 514/235.8 |
| 5,206,255 | 4/1993 | Ubasawa et al. | 514/374 |
| 5,264,589 | 11/1993 | Corey | 548/51 |
| 5,290,782 | 3/1994 | Suzuki et al. | 514/263 |
| 5,300,298 | 4/1994 | LaNoue | 424/442 |
| 5,322,847 | 6/1994 | Marfat et al. | 514/303 |
| 5,334,596 | 8/1994 | Hartman et al. | 514/301 |
| 5,422,350 | 6/1995 | Woolf | 514/252 |
| 5,434,150 | 7/1995 | Austel et al. | 514/228.5 |
| 5,447,933 | 9/1995 | Suzuki et al. | 514/263 |
| 5,470,579 | 11/1995 | Bonte et al. | 424/450 |
| 5,496,853 | 3/1996 | Shiota et al. | 514/469 |
| 5,631,260 | 5/1997 | Belardinelli et al. | 514/263 |

FOREIGN PATENT DOCUMENTS

| | | |
|---|---|---|
| 0389282 | 9/1990 | European Pat. Off. ...... C07D 473/06 |
| 0415456 | 3/1991 | European Pat. Off. . |
| 417790 | 3/1991 | European Pat. Off. . |
| 0435811 | 7/1991 | European Pat. Off. ...... C07D 473/04 |
| 0470805 | 2/1992 | European Pat. Off. . |
| 0497564 | 8/1992 | European Pat. Off. . |
| 0511865 | 11/1992 | European Pat. Off. . |
| 0536713 | 4/1993 | European Pat. Off. ...... C07D 263/34 |
| 0590919 | 4/1994 | European Pat. Off. ...... C07D 473/06 |
| 0619316 | 10/1994 | European Pat. Off. . |
| 0675124 | 10/1995 | European Pat. Off. . |
| 835818 | 2/1961 | France . |
| 1548252 | 12/1968 | France . |
| 51-54587 | 5/1976 | Japan . |
| 57-21375 | 2/1982 | Japan . |
| 1156978 | 6/1989 | Japan . |
| 559056 | 3/1993 | Japan . |
| 5105631 | 4/1993 | Japan . |
| 6211856 | 8/1994 | Japan . |
| 215948 | 10/1989 | New Zealand . |
| 1077689 | 8/1967 | United Kingdom . |
| 1498705 | 1/1978 | United Kingdom . |
| 1561005 | 2/1980 | United Kingdom ......... C07D 473/28 |
| 2041359 | 9/1980 | United Kingdom . |
| 1580782 | 12/1980 | United Kingdom ......... C07D 473/06 |
| 2091249 | 7/1982 | United Kingdom . |
| 8601724 | 3/1986 | WIPO . |
| 8706576 | 4/1986 | WIPO . |
| 8805306 | 7/1988 | WIPO . |
| 9100858 | 1/1991 | WIPO . |
| 9205175 | 4/1992 | WIPO . |
| 9205176 | 4/1992 | WIPO . |
| 9219594 | 11/1992 | WIPO . |
| 9307111 | 4/1993 | WIPO . |
| 9314081 | 7/1993 | WIPO . |
| 9314082 | 7/1993 | WIPO . |
| 9315044 | 8/1993 | WIPO . |
| 9315045 | 8/1993 | WIPO . |
| 9319747 | 10/1993 | WIPO . |
| 9325517 | 12/1993 | WIPO . |
| 9402465 | 2/1994 | WIPO . |
| 9410118 | 5/1994 | WIPO . |
| 9412461 | 6/1994 | WIPO . |
| 9414742 | 7/1994 | WIPO . |
| 9414800 | 7/1994 | WIPO . |
| 9420446 | 9/1994 | WIPO . |
| 9420455 | 9/1994 | WIPO . |
| 9420460 | 9/1994 | WIPO . |
| 9422859 | 10/1994 | WIPO . |
| 9424133 | 10/1994 | WIPO . |
| 95-00516 | 1/1995 | WIPO . |
| 9520589 | 8/1995 | WIPO . |
| 9523148 | 8/1995 | WIPO ......... C07D 473/06 |
| 9636638 | 11/1996 | WIPO ......... C07D 473/06 |
| 9712887 | 4/1997 | WIPO ......... C07D 473/00 |
| 9712888 | 4/1997 | WIPO . |
| 9749702 | 12/1997 | WIPO . |

OTHER PUBLICATIONS

"Phosphodiesterase inhibitors: new opportunities for the treatment of asthma", Theodore J. Torphy, Bradley J. Undem, *Thorax* 1991; 46:512–523.

"Novel phosphodiesterase inhibitors for the therapy of asthma", Theodore J. Torphy, George P. Livi and Siegfried B. Christensen, DN&P 6(4), May 1993 pp. 203–214.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, pp. 69–92.

"Identification, characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W.P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future, 1992, 17(9):799–807.

"Could isoenzyme–selective phosphodiesterase inhibitors render bronchodilator therapy redundant in the treatment of bronchial asthma?", Mark A. Giembycz, Biochemical Pharmacology, 1992, vol. 43, No. 10 pp. 2041–2051.

"Differential pharmacologic sensitivity of cyclic nucleotide phosphodiesterase isozymes from cardiac muscle, arterial and airway smooth muscle", Paul J. Silver, Linda T. Hamel, Mark H. Perrone, Ross G. Bently, Cynthia R. Bushover and Dale B. Evans, European Journal of Pharmacology, 150 (1988) 85–94, Elsevier.

"The pharmacology and therapeutic use of theophylline", Miles Weinberger, M.D., The Journal of Allergy and Clinical Immunology, vol. 73, No. 5, Part 1, 525–544.

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

"The Synthesis of Some 6 Thioxanthines", K.R.H. Wooldrige and R. Slack, J. Chem. Soc. 1962, Annex IV:1863–1868.

Enoki Chemical Abstracts, vol. 85, No. 1 (Jul. 9, 1976) 5692s.

Enoki Chemical Abstracts, vol. 84, No. 25 (Jun. 21, 1976) 180299v.

Aida Chemical Abstracts, vol. 86, No. 7 (Feb. 14, 1977) 43746r.

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

Chemical Abstracts 103: 37354, 1985 (Nagarajan).

Chemical Abstracts 116: 255335, 1992 (Bender).

Itaya, *Tetrahedron Letters*, vol. 23, No. 21 (1982), pp. 2203–2204.

Chemical Abstracts 88: 51054, 1977 (Ninomiya).

Chemical Abstracts, vol. 82 (19) May 12, 1975, Abstract #125358x (Kazimierczok).

Chemical Abstracts 114: 246982, 1990 (Naruto).

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Chemical Abstracts 92: 6207, 1977 (Pirisino).

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

G.T. Rogers and T.L.V. Ulbricht, Synthesis of 3–Methylisoguanine (6–amino–3–methylpurin–2(3H)–one), J. Chem. Soc. (C), pp. 2364–2366.

Chemical Abstracts 116:173873 (1979) Girshovich.

J. A. Montgomery, et al., "Synthesis of Potential Anticancer Agents. XIX. 2–Substituted $N^6$–Alkyladenines" (1959) J.A.C.S. vol. 81, pp. 3963–3967.

Chemical Abstracts 53:6243 (1957) Elion.

T. Fuji, et al. "3–Substituted Adenines. In Vitro Enzyme Inhibition and Antiviral Activity", (1979) Am. Chem. Soc., vol. 22, No. 2, pp. 126–129.

CA Selects: "Allergy & Antiallergic Agents", Issue 5, 1996, p. 17, (124:85064a).

Glüsenkamp, et al., "Tautomer–Specific Anti–(N–3–Substituted)–Adenine Antibodies: New Tools in . . . ", Angew. Chem. Int. Ed. Engl. 1993, 32, No. 11, pp. 1640–1641.

Reitz, et al., "Conformational Study of N–Substituted Adenines by Dynamic Proton NMR: Relatively . . . ", J. Org. Chem. 1990, 55, 5761–5766, pp. 5761–5766.

Leonard, et al., "Controlled Interaction between Nucleic Acid Bases. Intramolecular Stacking . . . ", Roger Adams Laboratory, School of Chemical Sciences, University of Illinois, 1972, pp. 4010–4016.

CA Select: "Anti–Inflammatory Agents & Arthritis" Issue 7, 1996, p. 26, Chem. Abstracts (124:46754).

Chem. Abstracts, 106:27814n (1987).

K.A. Jacobson, et al., "Sulfur–Containing 1,3–Dialkylxanthine Derivatives as Selective Antagonists at $A_1$–Adenosine Receptors", J. Med. Chem. 1989, vol. 32, pp. 1873–1879.

Cambridge Dictionary of Science and Technology, pp. 23–24 (1988).

5,864,037

METHODS FOR THE SYNTHESIS OF CHEMICAL COMPOUNDS HAVING PDE-IV INHIBITORY ACTIVITY

BACKGROUND OF THE INVENTION

The present invention relates to novel and improved methods for preparing adenine and purine derivatives and in particular the present invention relates to improved methods for preparing 3-substituted adenines and 3,8-di-substituted 6-aminopurine derivatives for use as phosphodiesterase inhibitors. The methods according to the invention provide a surprising and unexpectedly improved process that eliminates the need for thionation steps, and further helps avoid reactions under pressure with volatile aminating reagents in the preparation of cyclic nucleotide phosphodiesterase inhibitors.

Cyclic nucleotide phosphodiesterases (PDE's) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-cyclic monophosphate (cAMP) or guanosine 3',5'-cyclic monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article by Theodore J. Torphy, et al., "Novel Phosphodiesterases Inhibitors For The Therapy Of Asthma", Drug News & Prospectives, 6(4) May 1993, pages 203–214. The PDE enzymes can be grouped into five or more families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and possesses positive inotropic activity. PDE IV is cAMP specific, and possesses airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited.

It has previously been shown that the 3,8-di-substituted 6-thioxanthine derivatives as described in EP-A-0256692 exhibit enhanced bronchodilator and anti-inflammatory activity compared to the corresponding xanthine derivatives. Transformation of these 6-thioxanthine derivatives to the corresponding isoguanines substantially reduces the bronchodilator and anti-inflammatory activity in certain tests.

A different preparation of 3-methyl-6-dimethyl amino-3H-purine, 3-benzyl-6-methyl amino-3H-purine and 3-benzyl-6-isopropyl amino-3H-purine was reported in J. Org. Chem., 55, 5761–5766 (1990). No biological activity was disclosed for these compounds.

PDE IV (and possibly PDE V) is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous. It appears that selective PDE IV inhibitors should be more effective with fewer side effects than theophylline. Clinical support has been shown for this hypothesis. Attempts have therefore been made to find new compounds having more selective and improved PDE IV inhibition.

It has been shown in published international patent application WO 95/00516 (assigned to Euro-Celtique, S. A. and incorporated by reference in its entirety herein) that the analogous transformation of 3 and 3,8-di-substituted thiohypoxanthines into the corresponding purine derivatives gives compounds having PDE IV inhibitory activity comparable to or in some cases greater than 6-thioxanthine derivatives of EP-A-0256692.

WO 95/00516 discloses that 3- and 3,8-substituted 6-aminopurine derivatives possess potent PDE IV inhibitory and related antiinflammatory activity. However, the synthetic methods reported in that publication for the preparation of the 3- and 3,8-substituted 6-aminopurine derivatives of interest require a thionation step and require that the reaction be conducted under pressure in order to contain the necessary low boiling amines, both of which requirements create economic and processing inefficiencies during synthesis of these desirable compounds on a larger scale.

SUMMARY OF THE INVENTION

A primary object of the present invention is to provide new methods for the synthesis of compounds which are PDE IV inhibitors.

Another object of the present invention is to provide an improved method of synthesizing compounds which are PDE IV inhibitors without the need for a thionation step and without the need for a pressure reactor.

Further objects of this invention will become apparent from a reading of the following description.

With the above and other objects in view, the present invention relates in part to a novel group of 3-substituted and 3,8-di-substituted 6-amino purine derivatives having bronchodilator and/or anti-inflammatory activity.

DETAILED DESCRIPTION OF THE INVENTION

The instant invention involves the preparation of compounds of Formula IV from compounds of Formula I in three steps with a marked improvement in the ease of carrying out the reactions. The process is best illustrated in the following reaction scheme (Scheme A):

Scheme A

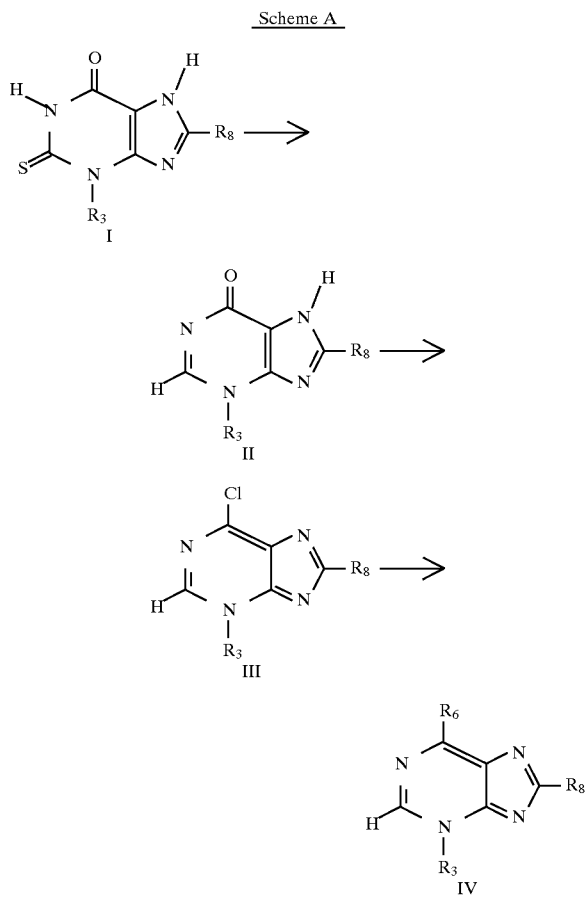

wherein:

$R_6$ is $N(R_{6a})(R_{6b})$ or a $C_3$–$C_8$ ring containing from one to three nitrogen atoms, from zero to two oxygen atoms, up to two sulfur atoms, optionally substituted with hydroxy, alkoxy, $C_{3-6}$ cycloalkoxy, $CO_2H$, $CONH_2$, =NOH, =NOCONH$_2$, (hydroxy) carbamido, =O;

$R_3$ represents an $C_{2-8}$ alkyl which is unbranched or branched and unsubstituted or substituted with OH, alkoxy, $C_{3-6}$ cycloalkoxy, halogen, =NOH, =NOCONH$_2$, (hydroxy)carbamido or =O;

$C_{3-8}$ cycloalkyl which is unsubstituted or substituted with OH, alkoxy, $C_{3-6}$ cycloalkoxy, halogen, =NOH, =NOCONH$_2$,(hydroxy)carbamido or =O; $C_{4-8}$ cycloalkylalkyl wherein the cycloalkyl portion is unsubstituted or substituted with OH, alkoxy, $C_{3-6}$ cycloalkoxy, halogen, =NOH, =NOCONH$_2$, or =O; aryl or benzyl which is optionally unsubstituted or substituted with OH, alkoxy, halogen, =NOH, =NOCONH$_2$,(hydroxy)carbamido or =O; $C_{4-8}$ cycloalkylalkyl wherein the cycloalkyl portion is unsubstituted or substituted with OH, alkoxy, $C_{3-6}$ cycloalkoxy, halogen, =NOH, =NOCONH$_2$, or =O; aryl or benzyl which is optionally unsubstituted or substituted with halogen, —NH$_2$, alkylamino, dialkylamino, optionally substituted carbamyl, —OH, $C_1$–$C_6$ alkoxy, $C_3$–$C_8$ cycloalkoxy, C=NOH, C=NOCONH$_2$,CH-(hydroxy) carbamido $C_1$–$C_8$ alkyl, phenyl or benzyl; ar($C_{1-4}$)alkyl; heterocyclyl; heterocyclyl ($C_1$–$C_4$)alkyl; heteroaryl; and heteroar ($C_{1-4}$)alkyl;

$R_8$ represents H or a $C_{1-8}$ alkyl which is unbranched or branched and unsubstituted or substituted with OH, alkoxy, $C_{3-6}$ cycloalkoxy, halogen, =NOH, =NOCONH$_2$, (hydroxy)carbamido or =O; $C_{3-8}$ cycloalkyl which is unsubstituted or substituted with OH, alkoxy, $C_{3-6}$ cycloalkoxy, halogen, =NOH, =NOCONH$_2$,(hydroxy) carbamido or =O; $C_{4-8}$ cycloalkylalkyl wherein the cycloalkyl portion is unsubstituted or substituted with —OH, alkoxy, $C_{3-6}$ cycloalkoxy, halogen, =NOH, =NOCONH$_2$, (hydroxy)carbamido or =O; aryl which is unsubstituted or substituted with halogen, —NH$_2$, alkylamino, dialkylamino, optionally substituted carbamyl, —OH, $C_1$–$C_6$ alkoxy, $C_3$–$C_8$ cycloalkoxy, C=NOH, C=NOCONH$_2$, CH-(hydroxy)carbamido $C_1$–$C_8$ alkyl, phenyl or benzyl; ar ($C_{1-4}$)alkyl; heterocyclyl; heterocyclyl ($C_1$–$C_4$)alkyl; heteroaryl; and heteroar($C_{1-4}$)alkyl; and $R_{6a}$ and $R_{6b}$ are independently selected from an H, a $C_{1-8}$ alkyl which is unbranched or branched and unsubstituted or substituted with OH, alkoxy, $C_{3-6}$ cycloalkoxy, halogen, =NOH, =NOCONH$_2$, or (hydroxy)carbamido =O; $C_{3-8}$ cycloalkyl which is unsubstituted or substituted with —OH, alkoxy, $C_{3-6}$ cycloalkoxy, halogen, =NOH, =NOCONH$_2$, (hydroxy) carbamido or =O; $C_{4-8}$ cycloalkylalkyl wherein the cycloalkyl portion is unsubstituted or substituted with —OH, alkoxy, $C_{3-6}$ cycloalkoxy, halogen, =NOH, =NOCONH$_2$, (hydroxy) carbamido or =O; aryl which is unsubstituted or substituted with halogen, —NH$_2$, alkylamino, dialkylamino, optionally substituted carbamyl, —OH, $C_1$–$C_6$ alkoxy, $C_3$–$C_8$ cycloalkoxy, C=NOH, C=NOCONH$_2$, CH-(hydroxy) carbamido $C_1$–$C_8$ alkyl, phenyl or benzyl; ar($C_{1-4}$)alkyl; heterocyclyl; heterocyclyl ($C_1$–$C_4$)alkyl; heteroaryl; and heteroar($C_{1-4}$)alkyl; —NR$_{6a}$ R$_{6b}$, together can form a 5-membered or 6-membered ring, which may be substituted or unsubstituted and optionally contains up to two additional hetero atoms; or R$_{6a}$ and R$_{6b}$ may form a 3 to 8 atom mono or bicyclic carbocyclic ring containing from one to three nitrogen atoms, from zero to two oxygen atoms, up to two sulfur atoms, optionally substituted with hydroxy, alkoxy, $C_{3-6}$ cycloalkoxy, $CO_2H$, $CONH_2$, =NOH, =NOCONH$_2$, (hydroxy) carbamido, =O.

In one preferred class of compounds of Formula IV $R_3$ represents a $C_{1-8}$ alkyl group; $R_{6a}$ represents a hydrogen atom, a $C_{1-8}$ alkyl group or a heteroaryl($C_1$–$C_4$)alkyl group; $R_{6b}$ represents a Hydrogen atom; and $R_8$ represents a hydrogen atom, a $C_{3-7}$ cycloalkyl group or a $C_{1-8}$ alkyl group.

In another preferred class of compounds of Formula IV $R_3$ is a $C_{1-5}$ alkyl group, a ar($C_{1-4}$)alkyl group or a $C_{3-7}$ cycloalkyl group; $R_{6a}$ represents a heteroaryl($C_1$–$C_4$)alkyl group; $R_{6b}$ represents a Hydrogen atom; and $R_8$ represents a $C_{1-8}$ alkyl group.

In a further preferred class of compounds $R_3$ is propyl, unsubstituted benzyl or a cyclopropyl methyl group; $R_8$ is cyclopropyl or iso-propyl; $R_{6a}$ is methyl or ethyl; and $R_{6b}$ is a hydrogen atom.

Particularly preferred compounds prepared by the process of the present invention include: 3-Benzyl-6-ethylamino-3H-purine; 6-ethylamino-3-hexyl-3H-purine; 8-cyclopropyl-3-cyclopropylmethyl-6-ethylamino-3H-purine; 6-cyclopentylamino-8-cyclopropyl-3-propyl-3H-purine; 3-(3-cyclopentyloxy-4-methoxybenzyl)-6-ethylamino-8-isopropyl-3H-purine; 8-cyclopropyl-3-propyl-6-(4-pyridylmethylamino)-3H-purine; 6-cyclopentylamino-3-(3-cylcopentyloxy-4-methoxybenzyl)-8-isopropyl-3H-purine; 3-(4-chlorobenzyl)-6-ethylamino-8-isopropyl-3H-purine; 3-(4-chlorobenzyl)-6-cyclopentylamino-8-cyclopropyl-3H-purine; 3-(3-cyclopentyloxy-4-methoxybenzyl)-6-ethylamino-3H-purine; 3-benzyl-6-ethylamino-8-(1-methylethyl)-3H- purine; 3-ethyl-6-cyclopentylamino-8-cyclopropyl-3H-purine; 8-cyclopropyl-6-ethylamino-3-(3-methylbutyl)-3H-purine; 3-cyclohexylmethyl-8-cyclopropyl-6-ethylamino-3H-purine; 8-cyclopropyl-3-cyclopropylmethyl-6-ethylamino-3H-purine; 3-ethyl-6-ethylamino-8-(3-cyclopentyloxy-4-methoxybenzyl)-3H-purine; 3-butyl-8-cyclopropyl-6-ethylamino-3H-purine; 3-(4-chlorobenzyl)-6-cyclopropylamino-8-isopropyl-3H-purine; 6-amino-3-(4-chlorobenzyl)-8-isopropyl-3H-purine 8-cyclopropyl-6-ethylamino-3-propyl-3H-purine; 3-ethyl-6-cyclopentylamino-8-isopropyl-3H-purine; 6-amino-8-cyclopropyl-3-propyl-3H-purine; 8-cyclopropyl-6-cyclopropylamino-3-propyl-3H-purine; 6-cyclopentylamino-8-isopropyl-3-propyl-3H-purine; 6-(3-cyclopentyloxy-4-methoxybenzylamino)-8-cyclopropyl-3-propyl-3H-purine; 6-butylamino-8-cyclopropyl-3-propyl-3H-purine; 3-cyclopropylmethyl-8-isopropyl-6-ethylamino-3H-purine; 8-cyclopropyl-3-ethyl-6-propylamino-3H-purine; 6-cyclohexylamino-8-isopropyl-3-propyl-3H-purine; 3,8-diethyl-6-morpholino-3H-purine; 6-amino-3-(4-chlorobenzyl)-8-isopropyl-3H-purine, 6-amino-3-(3-cyclopentyloxy-4-methoxy-benzyl)-8-isopropyl-3H-purine; and pharmaceutically acceptable salts thereof For purposes of the present invention, as used herein, aryl is phenyl or naphthyl. A heterocyclyl group is a 5, 6 or 7 membered ring having from one to three nitrogen atoms, zero to two oxygen atoms, up to two sulfur atoms, and can be optionally substituted on the carbons or nitrogens of the heterocyclyl ring. An alkyl group may be a straight or branched chain hydrocarbon and may be substituted or unsubstituted. Some of the preferred substituent groups being methyl, ethyl, n-propyl, iso-propyl, n-butyl, isobutyl, isopentyl, hydroxy, alkoxy (for example methoxy or ethoxy), $C_{3-6}$ cycloalkoxy, halogen (for example fluorine, chlorine or bromine) and haloalkyl (for example trifluoromethyl).

A $C_{3-7}$ cycloalkyl group or the cycloalkyl moiety of a $C_{4-8}$ cycloalkylalkyl group may preferably be a cyclobutyl, cyclopropyl or cyclopentyl group but is preferably cyclopropyl or cyclopentyl. A $C_{4-8}$ cycloalkylalkyl group may be cyclopropylmethyl, cyclobutylmethyl, cyclopentylmethyl, cyclohexylmethyl or cycloheptylmethyl but is preferably cyclopropylmethyl or cyclopentylmethyl. The cycloalkyl or cycloalkylalkyl group may be substituted or unsubstituted. Suitable substituents include hydroxy, alkoxy (for example methoxy or ethoxy), $C_{3-6}$ cycloalkoxy, halogen (for example fluorine, chlorine or bromine) and haloalkyl (for example trifluoromethyl).

An heteroaryl group or the heteroaryl moiety of an heteroar($C_{1-4}$)alkyl group is preferably pyridyl. The heteroaryl moiety may be unsubstituted or substituted, for example, by a $C_{1-4}$ alkyl group (such as methyl), an electron-withdrawing substituent such as a halogen atom (for example fluorine or chlorine), nitro, or trifluoromethyl, or an electron-donating group such as alkoxy or cycloalkoxy. An ar($C_{1-4}$) alkyl group is preferably benzyl or substituted benzyl.

The heterocyclic moiety of a heterocyclo($C_{1-4}$)alkyl group may suitably contain one or more heteroatoms, such as oxygen or nitrogen, and is conveniently a morpholinyl group.

It is understood that when $R_{6a}$ and $R_{6b}$ together form a 5-membered or a 6-membered ring containing an additional hetero atom, the additional hetero atom is preferably nitrogen or oxygen. The ring formed by —$NR_{6a}R_{6b}$ may be unsubstituted or substituted for example by a $C_{1-4}$ alkyl group (such as methyl or ethyl) hydroxy, alkyoxy, $C_{3-6}$ cycloalkoxy, or a halogen atom (such as fluorine or chlorine) and may optionally contain one or more units of unsaturation (double bond). Conveniently —$NR_{6a}R_{6b}$ may be a substituted or unsubstituted morpholine or piperazine ring.

The term "lower alkyl" is defined for purposes of the present invention as straight or branched chain alkyl radical having from 1 to 5 carbon atoms. Likewise, the term "alkoxy" is defined for purposes of the present invention as OR where R is a straight chain alkyl radical having from 1 to 6 carbon atoms, or a branched or cyclic alkyl radical having from 3 to 6 carbon atoms.

The compounds of the present invention, as well as their thioisoguanine and 2,6-dithioxanthine precursors have now been shown in WO 95/00516 to have PDE IV inhibitory activity using standard laboratory tests such as enzyme analysis, the guinea pig tracheal smooth muscle assay and PAF skin oedema and arachidonic acid mouse ear oedema tests and lymphocyte proliferation. These compounds may also find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

Accordingly, the invention is also directed to providing a compound of the invention or a pharmaceutically acceptable salt thereof for use in medicine, in particular for the treatment of conditions where a PDE IV inhibitory effect is indicated (for example chronic obstructive airway disease).

In particular, the invention further provides for improved methods for the manufacture of PDE IV inhibitory compounds or pharmaceutically acceptable salts thereof.

In a further aspect, the invention provides for a method of preparing compounds of the instant invention or pharmaceutically acceptable salts thereof by a novel process which avoids the thionation step and avoids the necessity of conducting the reaction under pressure for low boiling amine reagents. Accordingly, the novel synthetic sequence produces PDE IV inhibitory compounds according to the present invention by replacing an oxy-moiety with a chlorine, followed by substitution of the chlorine group by a desired amine substituent.

The active ingredient, produced as described herein, is preferably part of a pharmaceutical formulation, conveniently in unit dose form.

According to a further aspect the invention provides a pharmaceutical composition comprising at least one compound of Formula IV, or a pharmaceutically acceptable salt thereof, formulated for administration by a convenient route. The pharmaceutical compositions of the invention can conveniently be formulated in a conventional manner together with one or more pharmaceutically acceptable carriers or excipients.

Compounds produced according to the methods of the invention may conveniently be formulated in dosage forms for oral and parenteral administration, or for administration by inhalation.

For oral administration suitable dosage forms include solid dosage forms such as tablets and capsules which may be prepared by conventional pharmaceutical means with pharmaceutically acceptable excipients such as binders (for example starch or hydroxy propyl methyl cellulose), lubricating agents (such as magnesium stearate or talc), sweetening agents or lubricating agents. Liquid dosage forms which may be used include solutions, syrups or suspensions which may be prepared by conventional means with pharmaceutically acceptable adjuvants such as wetting agents, suspending agents, emulsifying agents and flavoring or perfuming agents.

For parenteral administration the compounds produced by the methods of the invention may conveniently take the form of sterile aqueous or non-aqueous solutions, suspensions or emulsions which may contain stabilizing, suspending or dispersing agents. Compositions may also be in the form of solid compositions such as powders which may be reconstituted with a suitable vehicle such as sterile water or other sterile injectable medium before use.

For administration by inhalation, the active ingredient may be delivered via an aerosol or nebulizer. The active ingredient may be present as a solid, a suspension or a solution.

In addition, when the compounds produced according to the methods of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Oxol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

The dose of the compounds of the present invention is dependent upon the affliction to be treated, the severity of the symptoms, the route of administration, the frequency of the dosage interval, the presence of any deleterious side-effects, and the particular compound utilized, among other things.

The dose of the active ingredient administered will depend on the particular compound used, the condition of the patient, the frequency and route of administration and the condition to be treated. The compounds of the invention may conveniently be administered one or more times, for example, 1 to 4 times per day. A proposed dose of the compounds of the invention is 1 to 10 mg/kg body weight, preferably 100 mg to 1000 mg per day.

The present invention is an improvement over the synthetic pathway disclosed in Schemes B1 and B2 (FIG. 3A, Scheme I of WO95/00516) as shown below:

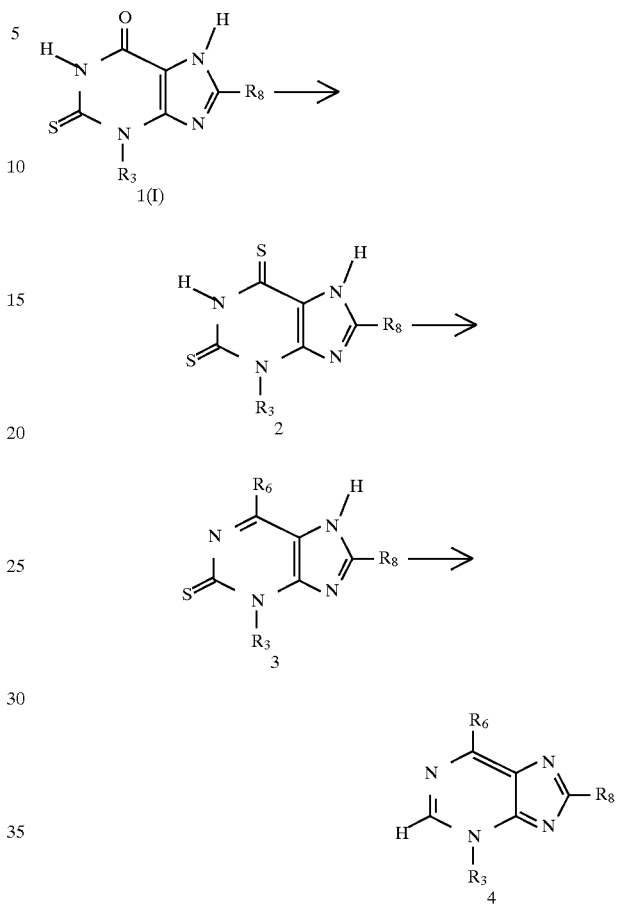

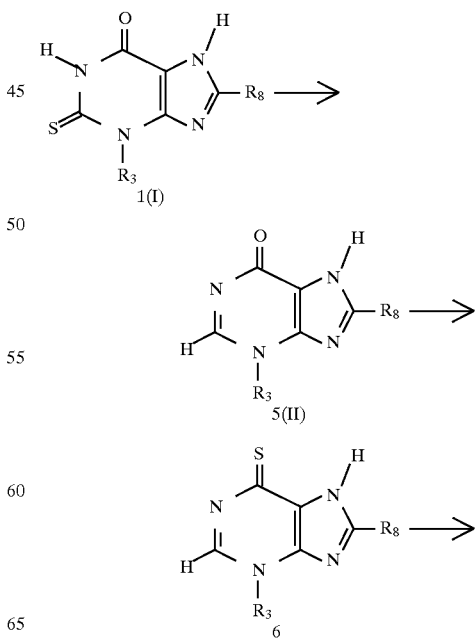

-continued
Scheme B2

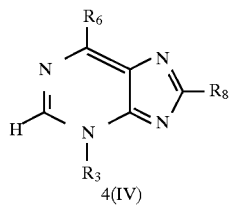

4(IV)

wherein the synthesis followed the route of 1 (I)→2→3→4 (Scheme B1) and 1→5 (II)→6→4 (IV) (Roman numerals in parenthesis indicate formulas as described herein). The steps 2→3 and 6→4 (product) are required to be conducted under pressure in order to keep the low boiling amine compounds in the reaction mixture. This is both inconvenient and adds significant costs to the synthesis of these compounds.

Surprisingly, it has now been found that this process can be greatly improved by bypassing the thiation step and conducting an alternative reaction as indicated by Scheme A.

Thus, in one of the preferred reaction pathways the 2-thio-6-oxy compounds of Formula I are reacted with Raney nickel to remove the thio-moiety to provide hypoxanthine, Formula II, which in turn is reacted with a halogenating reagent capable of replacing the oxo-moiety with a halogen, to produce the corresponding novel intermediate 6-halopurine compounds of Formula III. The 6-halopurine intermediate is in turn reacted with an amine to replace the halogen with an amino group to provide the corresponding substituted aminopurine compound of Formula IV.

According to the general process of the invention, compounds of Formula IV may be prepared by the synthetic scheme outlined in Scheme A above. The first step consists of dethionation of a compound of Formula I, wherein $R_3$ and $R_8$ are as defined earlier for Formula IV, with an effective amount of a dethionating agent, such as Raney nickel, to give a compound of Formula II. A compound of Formula II wherein $R_3$ and $R_8$ are as defined earlier for Formula IV, unless otherwise indicated, is then reacted with an effective halogenating agent, such as phosphorous oxychloride or thionyl chloride, to provide compounds of Formula III.

Compounds of Formula III, in turn, are then reacted with an effective aminating agent to produce compounds of Formula IV wherein the chlorine group is replaced by an amine group as represented by $R_6$ and where $R_3$, $R_6$ and $R_8$ are as defined earlier. Aminating agents, such as ethylamine or ammonia, that are known to be effective may be used under appropriate conditions.

The corresponding 2-thioxanthines, of Formula I, may in turn be prepared according to methods known in the art (see, for example, Arch Pharm 244 11–20 (1906) and J. Org. Chem., 27, 2478–2491 (1962)).

Compounds of Formula II are synthesized by reacting a 5% to 20% solution of a 2-thioxanthine of Formula I in a $C_{1-5}$ alcohol or water as alkaline salt is treated portionwise with Raney-nickel at a temperature ranging from 10° C. to 120° C., preferably at the reflux temperature of the solvent when ethanol or propanol is the solvent or at ambient temperature as sodium salt in water.

The reaction of a compound of Formula II with a effective halogenating agent may be conducted in a suitable reaction medium at a temperature ranging from about 10° C. to about 150° C., preferably ranging from about 50° C. to about 100° C. and more preferably at about 70° C. Suitable solvents include toluene, $CHCl_3$, $CH_2Cl_2$, DMF, DMA, dimethoxy ethane, THI, DMSO, ethylether, and the like. The halogenating agent replaces the oxy moiety with a halogen such as chlorine fluorine, iodine, and bromine, with chlorine being the preferred halogen. Effective halogenating agents include thionyl chloride, phosphorus oxychloride, phosphorus tribromide, and phosphorus trichloride.

In one aspect of the invention, the reaction to synthesize a chloro-substituted purine compound of Formula III is conducted in a suitable reaction medium, that contains hypoxanthine in a concentration ranging from about 0.1M to about 1.0M, or more, preferably the concentration of hypoxanthine being about 0.25M, and a chlorinating reagent e.g., phosphorus oxychloride at a temperature ranging from about −10° C. to about 150° C., preferably from about 50° C. to about 100° C., the more preferred temperature for this reaction being about 70° C.

Synthesis of amino-substituted purines (amino-purines), compounds of Formula IV, is accomplished by reacting halopurines, of Formula III, with a suitable amine. In one aspect of the invention a chloropurine, of Formula III, is present in a reaction medium at a concentration ranging from about 0.1M to about 1.0M, preferably at about 0.5M with aqueous ethylamine. The concentration of the ethylamine ranging up to about 20 time, or more, that of the chloropurine compound of Formula III. The reaction may be conducted at temperatures ranging from about 0° C. to about 100° C. or more. The reaction is typically conducted at ambient temperature.

Simply by way of example, the novel reaction process according to the invention can be used to make the following compounds, derivatives and/or homolog thereof:
3,8-Diethyl-6-morpholino-3H-purine;
8-(3-cyclopentyloxy-4-methoxybenzyl)-3-ethyl-6-ethylamino-3H-purine hydrochloride;
3-(3-cyclopentyloxy-4-methoxybenzyl)-6-ethylamino-8-isopropyl-3H-purine hydrochloride;
3-(3-Cyclopentyloxy-4-methoxybenzyl)-6-ethylamino-3H-purine hydrochloride;
8-Cyclopropyl-6-(4-pyridylmethyl-amino)-3-propyl-3H-purine dihydrochloride;
6-Cyclopentylamino-8-cyclopropyl-3-propyl-3H-purine hydrochloride;
8-Cyclopropyl-3-ethyl-6-ethylamino-3H-purine;
8-Cyclopropyl-3-ethyl-6-propylamino-3H-purine; and
6-amino-3(4-chlorobenzyl)-8-isopropyl-3H-purine;

Pharmaceutically acceptable salts of the compounds synthesized by the novel process of this invention can be prepared by methods known to one skilled in the art.

The following examples illustrate various aspects of the present invention and are not to be construed to limit the claims in any manner whatsoever.

EXAMPLE 1

8-Cyclopropyl-3-ethyl-6-ethylamino-3H-purine
(I) 6-Chloro-8-cyclopropyl-3-ethyl-3H-purine 0.41 g (2 mM) of hypoxanthine were refluxed with 8 ml of phosphorus oxychloride for 20 minutes. The reaction mixture was evaporated in vacuo to dryness. The residue was taken up in dichloromethane and extracted with sodium bicarbonate solution. The organic phase was then evaporated to dryness: 0.45 g (100%) of crude 6-chloropurine with mp 140°–145° C.

(ii) 8-Cyclopropyl-3-ethyl-6-ethylamino-3H-purine

A solution of 0.42 g (1.9 mM) of 6-chloropurine in 5 ml of THF was added to 0.61 ml (7.6 mM) of aqueous 70% ethylamine. After 1.5 hours of stirring, the reaction mixture was evaporated in vacuo to dryness. The residue was taken up in dichloromethane and extracted with sodium bicarbonate solution. The organic phase was evaporated to dryness: 0.49 g (111%) of crude aminopurine, which was dissolved in 5 ml of methanol and treated with 2.0 ml of 1M methanolic HCL (prepared from 32% HCL). The solution was treated with charcoal (5%), filtered and evaporated to dryness. The residue was then suspended in acetone and the crystals collected: 0.43 g (84.3%) of purine hydrochloride with mp 210°–2° C.

EXAMPLE 2

8-Cyclopropyl-3-ethyl-6-propylamino-3H-purine
(I) 6-chloro-8-cyclopropyl-3-ethyl-3H-purine
This compound was prepared by the general procedure outlined in Example 1.
(ii) 8-cyclopropyl-3-ethyl-6-propylamine-3H-purine
A solution of 0.10 g (0.4 mM) of 6-chloropurine in 5 ml of THF was treated with 1 ml of propylamine. After 0.5 hours, the reaction mixture was evaporated to dryness, the residue was taken up in dichloromethane and extracted with 1N NaOH solution. The organic phase was evaporated to dryness, dissolved in 5 ml of methanol and treated with 1 ml methanolic HCL. The reaction mixture was then evaporated to dryness and crystallized from acetone: 0.70 g (46.7%) of purine hydrochloride with mp 185°–7° C.

EXAMPLE 3

3-(3-Cyclopentyloxy-4-methoxy-benzyl)-6-ethylamino-8-isopropyl-3H-purine
(I) 3-(3-Cyclopentyloxy-4-methoxy-benzyl)-8-isopropyl-hypoxanthine
4.15 g (10 mM) of 3-(3-Cyclopentyloxy-4-methoxy-benzyl)-8-isopropyl-2-thioxanthine was dissolved in 42 ml of 1N NaOH and treated with three portions of 3 g of Raney-nickel with 0.5 hour intervals. After a further 0.5 hour, the nickel was filtered off and the solution acidified with 8 ml of 5N HCl to pH 3 and then neutralized with sodium bicarbonate solution to pH 7. The solid was collected, washed and dried: 3.62 g (94.5%) of hypoxanthine having a melting point of 243°–4° C.
(ii) 6-Chloro-3-(3-cyclopentyloxy-4-methoxy-benzyl)-8-isopropyl-3H-purine
1.19 g (5 mM) of hypoxanthine was heated in about 20 ml of phosphorus oxychloride for about 0.5 hour at about 65°–70° C. bath temperature. The reaction mixture was evaporated in vacuo and repeated twice with toluene. The yellow gum (3.33 g/162%) was then used directly for the following step.
(iii) 3-(3-Cyclopentyloxy-4-methoxy-benzyl)-6-ethylamino-8-isopropyl-3H-purine
The crude chloropurine (5 mM) was dissolved in about 10 ml of THF and added to about 20 ml (250 mM) of aqueous 70% ethylamine below 30° C. After about 1 hour of stirring, the mixture was evaporated to dryness, the residue taken up in about 60 ml of dichloromethane and extracted with about 1N NaOH solution (pH 13). The organic phase was evaporated to dryness, the residue (2.05 g/100%) dissolved in about 10 ml of methanol and treated with about 5.5 ml of methanolic HCL (from 32% HCL). The solution was then evaporated to dryness, the residue suspended in hot ethyl acetate and the solid collected: 1.83 g (82.1%) of purine hydrochloride with a melting point of 205°–7° C.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

What is claimed is:
1. A process for the preparation of a compound of Formula IV having the structure:

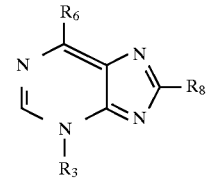

IV wherein
$R_6$ is $N(R_{6a})(R_{6b})$;
$R_3$ represents a $C_{2-8}$ alkyl which is unbranched or branched and unsubstituted or substituted with OH, alkoxy, $C_{3-6}$ cycloalkoxy, halogen, =NOH, =NOCONH$_2$, (hydroxy)carbamido or =O; $C_{3-8}$ cycloalkyl which is unsubstituted or substituted with OH, alkoxy, $C_{3-6}$ cycloalkoxy, halogen, =NOH, =NOCONH$_2$, (hydroxy)carbamido or =O; $C_{4-8}$ cycloalkylalkyl wherein the cycloalkyl portion is unsubstituted or substituted with OH, alkoxy, $C_{3-6}$ cycloalkoxy halogen, =NOH, =NOCONH$_2$, or =O; aryl or benzyl which is optionally unsubstituted or substituted with halogen, —NH$_2$, alkylamino, dialkylamino, carbamyl, —OH, $C_1$–$C_6$ alkoxy, $C_3$–$C_8$ cycloalkoxy, CH=NOH, CH=NOCONH$_2$, $C_1$–$C_8$ alkyl, phenyl or benzyl; ar($C_{1-4}$)alkyl; a heterocyclyl group, said heterocyclyl group being a 5-, 6- or 7-membered ring having from one to three nitrogen atoms, zero to two oxygen atoms, and up to two sulfur atoms, said carbons or nitrogens of said ring optionally substituted with $C_{1-4}$ alkyl, halogen, CF$_3$, alkoxy or cycloalkoxy; heterocyclyl ($C_1$–$C_4$) alkyl wherein the heterocyclyl moiety is a 5-, 6- or 7-membered ring having from one to three nitrogen atoms, zero to two oxygen atoms, and up to two sulfur atoms, said carbons or nitrogens of said ring optionally substituted with $C_{1-4}$ alkyl, halogen, CF$_3$, alkoxy or cycloalkoxy;
$R_8$ represents H or a $C_{1-8}$ alkyl which is unbranched or branched and unsubstituted or substituted with OH, alkoxy, $C_{3-6}$ cycloalkoxy, halogen, =NOH, =NOCONH$_2$, (hydroxy)carbamido or =O; $C_{3-8}$ cycloalkyl which is unsubstituted or substituted with OH, alkoxy, $C_{3-6}$ cycloalkoxy, halogen, =NOH, =NOCONH$_2$, (hydroxy)carbamido or =O; $C_{4-8}$ cycloalkylalkyl wherein the cycloalkyl portion is unsubstituted or substituted with —OH, alkoxy, $C_{3-6}$ cycloalkoxy halogen, =NOH, =NOCONH$_2$, (hydroxy)carbamido or =O; aryl which is unsubstituted or substituted with halogen, —NH$_2$, alkylamino, dialkylamino, carbamyl, —OH, $C_1$–$C_6$ alkoxy, $C_3$–$C_8$ cycloalkoxy, CH=NOH, CH=NOCONH$_2$, $C_1$–$C_8$ alkyl, phenyl or benzyl; ar($C_{1-4}$)alkyl; a heterocyclyl group, said heterocyclyl group being a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy; heterocyclyl($C_1$–$C_4$)alkyl wherein the heterocyclyl moiety is a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy;

R$_{6a}$ and R$_{6b}$ are independently selected from H, C$_{1-8}$ alkyl which is unbranched or branched and unsubstituted or substituted with OH, alkoxy, C$_{3-6}$ cycloalkoxy, halogen, =NOH, =NOCONH$_2$, (hydroxy)carbamido or =O; C$_{3-8}$ cycloalkyl which is unsubstituted or substituted with —OH, alkoxy, C$_{3-6}$ cycloalkoxy, halogen, =NOH, =NOCONH$_2$, (hydroxy) carbamido or =O; C$_{4-8}$ cycloalkylalkyl wherein the cycloalkyl portion is unsubstituted or substituted with —OH, alkoxy, C$_{3-6}$ cycloalkoxy, halogen, =NOH, =NOCONH$_2$, (hydroxy) carbamido or =O; aryl which is unsubstituted or substituted with halogen, —NH$_2$, alkylamino, dialkylamino, —OH, C$_1$-C$_6$ alkoxy, C$_3$-C$_8$ cycloalkoxy, CH=NOH, CH=NOCONH$_2$, C$_1$-C$_8$ alkyl, phenyl or benzyl; ar(C$_{1-4}$)alkyl; a heterocyclyl group, said heterocyclyl group being a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, or alkoxy or cycloalkoxy; heterocyclyl(C$_1$-C$_4$) alkyl wherein the heterocyclyl moiety is a 5-, 6- or 7-membered ring having from one to three nitrogen atoms, zero to two oxygen atoms, and up to two sulfur atoms said carbons or nitrogens of said ring optionally substituted with alkyl, halogen, CF$_3$, alkoxy or cycloalkoxy; or N(R$_{6a}$)(R$_{6b}$) may together form a 3 to 8 atom ring containing from one to three nitrogen atoms, from zero to two oxygen atoms, and up to two sulfur atoms, optionally substituted with hydroxy, alkoxy, C$_{3-6}$ cycloalkoxy, CO$_2$H, CONH$_2$, =NOH, =NOCONH$_2$, (hydroxy) carbamido, =O; and which comprises:

(a) treating a compound of Formula I:

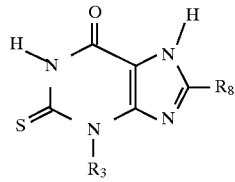

wherein R$_3$ and R$_8$ are as defined above, with an effective amount of a dethionating agent to produce a compound of Formula II:

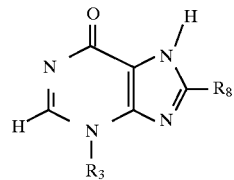

(b) treating a compound of Formula II, wherein R$_3$ and R$_8$ are as defined above, with an effective halogenating agent under conditions effective to produce a compound of Formula III:

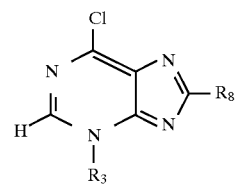

wherein R$_3$ and R$_8$ are as defined above; and (c) treating a compound of Formula III wherein R$_3$ and R$_8$ are as defined above with an effective aminating agent under conditions effective to produce a compound of Formula IV.

2. The process of claim 1, wherein

R$_3$ represents a C$_{2-8}$ alkyl, C$_{3-7}$ cycloalkyl, C$_{4-8}$ cycloalkylalkyl, aryl or ar(C$_{1-4}$)alkyl, a heterocyclcl group, said heterocyclyl group being a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy, or a heterocyclyl(C$_1$-C$_4$)alkyl group having a heterocyclyl moiety wherein the heterocyclyl moiety is a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy;

R$_{6a}$ represents a hydrogen atom, C$_{1-8}$ alkyl, C$_3$-C$_7$ cycloalkyl, C$_{4-8}$ cycloalkylalkyl, aryl, a heterocyclyl group, said heterocyclyl group being a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy; ar(C$_1$-C$_4$)alkyl group; or heterocyclyl (C$_{1-4}$) alkyl group having a heterocyclyl moiety wherein the heterocyclyl moiety is a 5-, 6- or 7-membered ring having from one to three nitrogen atoms, zero to two oxygen atoms, and up to two sulfur atoms said carbons or nitrogens of said ring optionally substituted with alkyl, halogen, nitro, CF$_3$, alkoxy or cycloalkoxy;

R$_{6b}$ represents a H, C$_{1-8}$ alkyl, C$_{3-7}$ cycloalkyl, C$_{4-8}$ cycloalkylalkyl, aryl or ar(C$_{1-4}$)alkyl group; or —NR$_{6a}$R$_{6b}$ together forms a 5-membered or 6-membered ring, which ring optionally contains up to two additional heteroatoms; and R$_8$ represents a hydrogen atom or a C$_{1-8}$ alkyl, C$_{3-7}$ cycloalkyl, C$_{4-8}$ cycloalkylalkyl, aryl, ar(C$_{1-4}$)alkyl, pyridyl or pyridyl(C$_{1-4}$)alkyl group.

3. The process of claim 2, wherein R$_3$ represents a C$_{2-8}$ alkyl group, an aryl, ar(C$_{1-4}$) alkyl group, a C$_{3-7}$ cycloalkyl group, a heterocyclycl group, said heterocyclyl group being a 5-, 6- or 7-membered ring having from one to three nitrogen atoms, zero to two oxygen atoms, and up to two sulfur atoms, said carbons or nitrogens of said ring optionally substituted with alkyl, halogen, CF$_3$, alkoxy or cycloalkoxy, or a heterocyclyl(C$_1$-C$_4$)alkyl having a heterocyclyl moiety wherein said heterocyclcl moiety is a 5-, 6- or 7-membered ring having from one to three nitrogen atoms, zero to two oxygen atoms, and up to two sulfur atoms, said carbons or nitrogens of said ring optionally substituted with alkyl, halogen, nitro, CF$_3$, alkoxy or cycloalkoxy.

4. The process of claim 2, wherein R$_{6a}$ represents a hydrogen atom, C$_{1-8}$ alkyl group, C$_3$-C$_7$ cycloalkyl group, benzyl or picolyl group and R$_{6b}$ represents a hydrogen atom.

5. The process of claim 2, wherein $R_8$ represents a hydrogen atom.

6. The process of claim 2, wherein $R_8$ represents a $C_{4-8}$ cycloalkylalkyl or $C_{3-7}$ cycloalkyl group.

7. The process of claim 6, wherein $R_8$ represents a cyclopropyl group.

8. The process of claim 2, wherein $R_8$ represents a $C_{1-8}$ alkyl group.

9. The process of claim 8, wherein $R_8$ represents an isopropyl group.

10. The process of claim 1, wherein a compound of Formula IV is selected from the group consisting of 6-ethylamino-3-hexyl-3H-purine; 3-hexyl-6-methylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-ethyl-6-methyl amino-3H-purine; 3-butyl-6-ethylamino-3H-purine; 3-butyl-8-cyclopropyl-6-ethylamino-3H-purine; 6-ethylamino-3-propyl-3H-purine; 8-cyclopropyl-6-ethylamino-3-propyl-3H-purine; 8-cyclopropyl-3-cyclopropylmethyl-6-ethylamino-3H-purine; 3-benzyl-6-ethylamino-3H-purine; 8-cyclopropyl-6-cyclopropylamino-3-propyl-3H-purine; 3-(2-methylbutyl)-6-(2-(piperazine-1-yl)ethylamino)-3H-purine; 3-cyclohexylmethyl-6-ethylamino-3H-purine; 3-benzyl-6-ethylamino-8-(1-methylethyl)-3H-purine; 3-cyclohexyl-methyl-8-cyclopropyl-6-ethylamino-3H-purine; 3-cyclopropylmethyl-8-isopropyl-6-ethylamino-3H-purine; 3-ethyl-8-isopropyl-6-benzylamino-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-(4-chlorobenzyl)-6-ethylamino-3H-purine; 3-(2-chlorobenzyl)-6-ethylamino-3H-purine; 3-(2-chlorobenzyl)-6-ethylamino-8-isopropyl-3H-purine; 6-benzylamino-8-cyclopropyl-3-propyl-3H-purine; 8-cyclopropyl-6-hexylamino-3-propyl-3H-purine; 8-cyclopropyl-3-propyl-6-(4-pyridylmethylamino)-3H-purine; 6-cyclopentylamino-8-cylopropyl-3-propyl-3H-purine; 6-butyl-amino-8-cyclopropyl-3-propyl-3H-purine; 8-cyclopropyl-6-(2-hydroxyethylamino)-3-propyl-3H-purine; 6-amino-8-cyclopropyl-3-propyl-3H-purine; 3-ethyl-6-cyclopentylamino-8-isopropyl-3H-purine; 6-cyclohexylamino-8-isopropyl-3-propyl-3H-purine; 6-cyclopentylamino-8-isopropyl-3-propyl-3H-purine; 3-ethyl-6-cyclopentylamino-8-cyclopropyl-3H-purine; 3-(4-chlorobenzyl)-6-cyclopentylamino-8-cyclopropyl-3H-purine; 6-cyclopentylamino-3-(3-cyclopentyloxy-4-methoxybenzyl)-8-isopropyl-3H-purine; 3-(2-chlorobenzyl)-6-cyclopentylamino-8-isopropyl-3H-purine; 8-cyclopropyl-6-diethylamino-3-propyl-3H-purine; 8-cyclopropyl-6-(3-pentylamino)-3-propyl-3H-purine; 6-ethylamino-8-isopropyl-3-(4-pyridylmethyl)-3H-purine; 3-ethyl-8-isopropyl-6-ethylamino-3H-purine; 3-ethyl-8-cyclopentyl-6-benzylamino-3H-purine; 3-ethyl-8-cyclopentyl-6-ethylamino-3H-purine; 3-cylcohexylmethyl-6-ethylamino-3H-purine; 3-cyclohexylmethyl-8-cyclopropyl-6-ethylamino-3H-purine; 8-cyclopropyl-6-ethylamino-3-(3-methylbutyl)-3H-purine; 8-cyclopropyl-3-ethyl-6-propylamino-3H-purine; 8-cyclopropyl-3-cyclopropylmethyl-6-ethylamino-3H-purine; 3-hexyl-6-methyl amino-3H-purine; 3-cyclopropylmethyl-8-isopropyl-6-ethylamino-3H-purine; 3-ethyl-8-isopropyl-6-benzylamino-3H-purine; 3-butyl-6-ethylamino-3H-purine; 3-butyl-8-cyclopropyl-6-ethylamino-3H-purine; 8-cyclopropyl-6-ethylamino-3-propyl-3H-purine; 8-cyclopropyl-6-cyclopropylamino-3-propyl-3H-purine; 3-(3-cyclopentyloxy-4-methoxy-benzyl)-6-ethylamino-8-isopropyl-3H-purine; 3-ethyl-6-ethylamino-8-(3-cyclopentyloxy-4-methoxy-benzyl)-3H-purine; 6-amino-3-(3-cyclopentyloxy-4-methoxy-benzyl)-8-isopropyl-3H-purine; 3,8-diethyl-6-morpholino-3H-purine; 6-amino-3-(4-chlorobenzyl)-8-isopropyl-3H-purine, 3-(4-chlorobenzyl)-6-cyclopropylamino-8-isopropyl-3H-purine; 3-(3-cyclopentyloxy-4-methoxybenzyl)-6-ethylamino-3H-purine; and 8-cyclopropyl-3-ethyl-6-ethylamino-3H-purine.

11. The process of claim 10, wherein a compound of Formula IV is selected from the group consisting of 3-(3-cyclopentyloxy-4-methoxybenzyl)-6-ethylamino-3H-purine; 3-(4-chlorobenzyl)-6-ethylamino-8-isopropyl-3H-purine; 3-(3-cyclopentyloxy-4-methoxy-benzyl)-6-ethylamino-8-isopropyl-3H-purine; 8-cyclopropyl-3-propyl-6-(4-pyridylmethylamino)-3H-purine; 6-amino-3(3-cyclopentyloxy-4-methoxy-benzyl)-8-isopropyl-3H-purine, and their pharmaceutically acceptable salts.

12. The process of claim 3, wherein $R_3$ represents a $C_{1-5}$ alkyl group.

13. The process of claim 4, wherein $R_{6a}$ represents ethyl or 4-picolyl, and $R_{6b}$ represents a hydrogen atom.

14. The process of claim 12, wherein $R_3$ represents propyl.

15. The process of claim 3, wherein $R_3$ represents substituted and unsubstituted benzyl.

16. The process of claim 3, wherein $R_3$ represents cyclopropylmethyl.

17. A process of claim 1 wherein (a) a compound of Formula I is treated with an effective amount of Raney-nickel to produce a compound of Formula II; (b) a compound of Formula II is treated with an effective amount of phosphorus oxychloride to produce a compound of Formula III; (c) a compound of Formula III is treated with an effective amount of ethylamine to produce a compound of Formula IV.

18. A process of claim 1, wherein the solvent for the reaction is selected from the group consisting of water, alcohol, methylene chloride, or hydrocarbons.

* * * * *